(12) United States Patent
Eutick

(10) Patent No.: US 9,522,214 B2
(45) Date of Patent: Dec. 20, 2016

(54) VISCOUS HAEMOSTATIC COMPOSITIONS AND METHOD OF TREATMENT

(71) Applicant: Eupharma Pty Ltd, New South Wales (AU)

(72) Inventor: Malvin Eutick, New South Wales (AU)

(73) Assignee: Eupharma PTY LTD, New South Wales (AU)

( * ) Notice: Subject to any disclaimer, the term of this patent is extended or adjusted under 35 U.S.C. 154(b) by 0 days.

(21) Appl. No.: 14/427,430

(22) PCT Filed: Sep. 12, 2013

(86) PCT No.: PCT/AU2013/001038
§ 371 (c)(1),
(2) Date: Mar. 11, 2015

(87) PCT Pub. No.: WO2014/043743
PCT Pub. Date: Mar. 27, 2014

(65) Prior Publication Data
US 2015/0238652 A1  Aug. 27, 2015

(30) Foreign Application Priority Data

Sep. 19, 2012  (AU) ................ 2012904082

(51) Int. Cl.

| | | |
|---|---|---|
| *A61K 33/06* | (2006.01) | |
| *A61K 33/26* | (2006.01) | |
| *A61K 33/32* | (2006.01) | |
| *A61K 33/36* | (2006.01) | |
| *A61K 45/06* | (2006.01) | |
| *A61L 15/18* | (2006.01) | |
| *A61L 15/44* | (2006.01) | |
| *A61L 24/02* | (2006.01) | |
| *A61L 24/00* | (2006.01) | |
| *A61K 33/38* | (2006.01) | |
| *A61L 26/00* | (2006.01) | |

(52) U.S. Cl.
CPC .......... *A61L 24/0031* (2013.01); *A61K 33/06* (2013.01); *A61K 33/26* (2013.01); *A61K 33/32* (2013.01); *A61K 33/38* (2013.01); *A61K 45/06* (2013.01); *A61L 15/18* (2013.01); *A61L 15/44* (2013.01); *A61L 24/0015* (2013.01); *A61L 24/02* (2013.01); *A61L 26/0004* (2013.01); *A61L 26/008* (2013.01); *A61L 26/0066* (2013.01); *A61L 2300/102* (2013.01); *A61L 2300/402* (2013.01); *A61L 2300/802* (2013.01); *A61L 2400/04* (2013.01)

(58) Field of Classification Search
CPC .... A61K 2300/00; A61K 33/06; A61K 33/26; A61K 33/32; A61K 33/38; A61K 45/06; A61L 15/18; A61L 15/44; A61L 2300/102; A61L 2300/402; A61L 2300/802; A61L 2400/04; A61L 24/0015; A61L 24/0031; A61L 26/0004; A61L 26/0066; A61L 26/008
See application file for complete search history.

(56) References Cited

U.S. PATENT DOCUMENTS

| | | | | |
|---|---|---|---|---|
| 4,889,844 A | * | 12/1989 | Silvetti, Sr. | ........ A61K 31/7004 424/672 |
| 5,011,693 A | * | 4/1991 | Whitefield | ............. A61K 33/06 424/435 |
| 5,575,995 A | | 11/1996 | Giovanni | |
| 7,122,578 B2 | * | 10/2006 | Martin | ................. A61K 31/315 424/400 |
| 2003/0226217 A1 | | 12/2003 | Bowes | |
| 2006/0051486 A1 | * | 3/2006 | Dowdell | ................. A61K 8/27 426/601 |

FOREIGN PATENT DOCUMENTS

WO    WO 2009/017757 A2    2/2009

OTHER PUBLICATIONS

Flick (Cosmetic and Toiletry Formulations 1997, 2nd Ed. vol. 6: pp. 214 and 335).*
"CRODAFOS™ CES—Hitting the target for more effective actives" CRODA Personal Care North America [retrieved on Oct. 4, 2012] [retrieved from Internet <URL: http://www.croda.com/home.aspx?d=content&s=157&r=401&p=2810> published on Jun. 30, 2011 as per Wayback Engine].

* cited by examiner

*Primary Examiner* — Ernst V Arnold
(74) *Attorney, Agent, or Firm* — Klarquist Sparkman, LLP

(57) ABSTRACT

A method of promoting haemostasis in a patient is provided by the administration, to the site of blood loss, of a viscous thixotropic haemostatic composition comprising an ionic precipitating agent, a fatty alcohol, an alcohol phosphate diester and one of an alkoxyether phosphate or a monoester phosphate of an alkoxylated fatty alcohol.

29 Claims, No Drawings

VISCOUS HAEMOSTATIC COMPOSITIONS AND METHOD OF TREATMENT

CROSS REFERENCE TO RELATED APPLICATIONS

This is the U.S. National Stage of International Application No. PCT/AU2013/001038, filed Sep. 12, 2013, which was published in English under PCT Article 21(2), which in turn claims the benefit of Australia Application No. 2012904082, filed Sep. 19, 2012. The Australia application is incorporated herein in its entirety.

FIELD OF THE INVENTION

The present invention relates to compositions comprising haemostatic agents and methods of treatment using same. In particular, although not exclusively, the invention relates to viscous thixotropic compositions (of haemostatic agents for topical targeted application to wounds.

BACKGROUND TO THE INVENTION

Haemostatic agents have been known for many years. A well know haemostatic agent, for example, is "Monsel's Solution", first described as a aqueous liquid by the French pharmacist Leon Monsel in 1852 and used during the Crimean War. The principal of its action is the presence of a ferric ion, which is a strong protein precipitant, causing coagulation which mechanically seals smaller blood vessels at a wound site.

Other solutions of polyvalent metal ions such as Ferric Chloride, Silver Nitrate, Silver Chloride, Aluminium Chloride Hexahydrate, Aluminium Sulphate and Aluminium Acetate are also utilised as haemostatic agents, and their mode of action is similar.

Monsel's Solution is applied by topical application to superficial cuts, wounds and abrasions and is commonly used to stem blood flow after punch biopsies, skin biopsies, and removal of localised skin lesions by curettage. Other uses of this haemostatic agent include as a styptic used in colposcopy, including following cervical biopsy and vulval biopsies, in shave excision, nail fold biopsy, nail matricectomy and cerumen removal. It also has use for minor wounds and abrasions or use in any location where a rapid and convenient cessation of blood flow is required. Its use is not limited to small wounds as it has also been successfully utilised as a coagulant in large exposed skin wounds. A use has been found to stop uterine bleeding without the loss of fertility (Disu S, Rebello L, Atalla R, "The Use of Interuterine Monsel's Solution in Severe Hemorrhage After Evacuation of Retained Products of Conception: A Case Report" Am. J Obstet. Gynecol; 2007 February: 196(2): p 6-7) and it has been found to be less painful and more effective in haemostasis after clot extraction from thrombosed external haemorrhoids than Silver Nitrate (Jetmore A B, Heryer J W, Conner W E, "Monsel's Solution: A kinder and Gentler Hemostatic", Dis Colon Rectum 1993; 36: 866-867). Dentists may use it during tooth extraction.

While Monsel's solution in its aqueous from is an effective haemostatic agent, it (or indeed other simple aqueous salts), is not entirely satisfactory in use. More particularly, it is a very acid solution and, because of its iron content, causes staining and other problems if it is spilled or runs off the wound onto surrounding tissues or, indeed, clothing. It must therefore be handled and applied with care. Additionally, because of its high concentration which approaches saturation, the solute is liable to crystallise out even on short term storage and especially if the solution is stored at low temperatures or allowed to evaporate.

Many commercial supplies include the warning to hold the styptic above 22° C. In some instances a "paste" is made of the Monsel's solution by allowing evaporation to take place on standing to provide the required viscosity. However, this is a very non-reproducible method and the crystallisation is not controllable.

Other salt solutions such as those of aluminium chloride hexahydrate in water or aqueous alcohol (ethanol or isopropyl alcohol) containing 20 to 70% w/v of the salt (calculated as the hydrated salt) are also used as haemostatic agents and have similar problems.

It would therefore be highly advantageous if a haemostatic agent could be provided that reduces and/or alleviates the problems with the existing products.

OBJECT OF THE INVENTION

It is an object of some embodiments of the present invention to provide consumers with improvements and advantages over the above described prior art, and/or overcome and alleviate one or more possible disadvantages of the prior art, and/or provide a useful commercial choice.

SUMMARY OF THE INVENTION

The present invention is predicated, at least in part, on the finding that a highly advantageous viscous, and thixotropic, haemostatic gel composition can be formed using known haemostatic solutions which, in the composition of the invention, become very much easier and more convenient to handle without impairing their haemostatic properties, by formulating them as gels or viscous thixotropic wax-like compositions. These compositions will be solid at room temperature but liquefy on touch or pressure, allowing them to be taken up onto or into a swab or applicator, kept solid during transfer and then become liquid again on pressing or swabbing onto the wound. They will set on the wound surface thus limiting spread to other unaffected surfaces which is important given the highly acidic nature of the preparations. These compositions include fatty alcohols, alcohol phosphate diesters and one of an alkoxyether phosphate or a monoester phosphate of an alkoxylated fatty alcohol.

According to a first aspect, the invention resides in a method of promoting haemostasis in a patient in need thereof including the step of administering to the site of blood loss a viscous thixotropic haemostatic composition comprising an ionic precipitating agent, a fatty alcohol, an alcohol phosphate diester and one of an alkoxyether phosphate or a monoester phosphate of an alkoxylated fatty alcohol.

According to a second aspect, there is provided a viscous thixotropic haemostatic gel composition for use in promoting haemostasis at a site of blood loss in a patient in need thereof wherein the viscous thixotropic haemostatic composition comprises an ionic precipitating agent, a fatty alcohol, an alcohol phosphate diester and one of an alkoxyether phosphate or a monoester phosphate of an alkoxylated fatty alcohol.

According to a third aspect, the invention resides in a viscous thixotropic haemostatic composition comprising (i) an ionic precipitating agent comprising a polyvalent metal ion wherein the metal is selected from the group consisting of iron, silver, aluminium, calcium, magnesium and manganese; (ii) a fatty alcohol; (iii) an alcohol phosphate diester; and (iv) one of an alkoxyether phosphate or a monoester phosphate of an alkoxylated fatty alcohol.

According to a fourth aspect, there is provided a use of a viscous thixotropic haemostatic composition comprising an ionic precipitating agent, a fatty alcohol, an alcohol phosphate diester and one of an alkoxyether phosphate or a monoester phosphate of an alkoxylated fatty alcohol in the manufacture of a medicament for the promotion of haemostasis at a site of blood loss in a patient.

According to a fifth aspect, the invention resides in a kit comprising the viscous thixotropic haemostatic composition of the third aspect and an applicator device.

According to a sixth aspect, the invention resides in a method of formulating the viscous thixotropic haemostatic composition of the third aspect including the step of combining an ionic precipitating agent comprising a polyvalent metal ion wherein the metal is selected from the group consisting of iron, silver, aluminium, calcium, magnesium and manganese with a fatty alcohol, an alcohol phosphate diester and one of an alkoxyether phosphate or a monoester phosphate of an alkoxylated fatty alcohol.

DETAILED DESCRIPTION OF THE INVENTION

According to a first aspect, the invention resides in a method of promoting haemostasis in a patient in need thereof including the step of administering to the site of blood loss a viscous thixotropic haemostatic gel composition comprising an ionic precipitating agent, a fatty alcohol, an alcohol phosphate diester and one of an alkoxyether phosphate or a monoester phosphate of an alkoxylated fatty alcohol.

The ionic precipitating agent can be any appropriate agent which can effect precipitation of proteins to cause haemostasis. Such agents may comprise cations selected from the group consisting of iron, silver, aluminium, calcium, magnesium, manganese and ammonium.

The relevant cations may be derived from salts of the metals and ammonium ion wherein the salts may be selected from the group consisting of chlorides, nitrates, sulphates and acetates. In some embodiments preferred salts may be selected from the group consisting of ferric chloride, iron sulphates, inclusive of ferric subsulphate, silver nitrate, silver chloride, aluminium chloride hexahydrate, aluminium sulphate and aluminium acetate. These agents are strong protein precipitants causing a coagulation which mechanically seals smaller blood vessels. The composition of the invention allows very targeted and controlled application of these agents to a wound site.

Preferably, the ionic precipitating agent is included in the composition of the invention as "Monsel's Solution". Monsel's Solution is commonly referred to as a ferric subsulphate solution (the formula often cited is $Fe_4(OH)_2(SO_4)_5$) and is formed by the oxidation of ferrous ferric sulphate with nitric and sulphuric acids. Monsel's solution typically includes from about 15% to about 25% w/v calculated as iron (III) of ferric sulphate, although the precise nature of the ferric ion is unknown. More preferably, the concentration of iron (III) is included from about 20% to 22%. However, lower concentrations may be used where a slower effect is acceptable, for example from about 5 to 15% w/v iron (III).

Preferably, the pH of this Monsel's solution should be below pH 0.5.

The fatty alcohol of the composition is preferably a long chain fatty alcohol wherein long chain is defined as comprising between a carbon chain, branched or unbranched, having between about 10 to 22 carbon atoms, preferably between 12 to 20 carbon atoms, more preferably between 14 to 20 carbon atoms. Such fatty alcohols include those selected from the group consisting of $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, and $C_{22}$ fatty alcohols. Particularly preferred fatty acids are selected from the group consisting of myristyl alcohol (1-tetradecanol), pentadecyl alcohol (1-pentadecanol, pentadecanol), cetyl alcohol (1-hexadecanol), heptadecyl alcohol (1-n-heptadecanol, heptadecanol), stearyl alcohol (1-octadecanol), nonadecyl alcohol (1-nonadecanol) and arachidyl alcohol (1-eicosanol).

In one preferred embodiment, the fatty alcohol is a mix of cetyl and stearyl alcohols. Preferably, the mix of cetyl and stearyl alcohols is in the form of cetostearyl alcohol (CAS-No. 67762-27-0) which is a commercially available product.

The alcohol phosphate diester of the composition is preferably a diester phosphate of a non-alkoxylated fatty alcohol having from about 12 to about 22 carbon atoms, preferably between 13 to 20 carbon atoms, more preferably between 14 to 18 carbon atoms. Such non-alkoxylated fatty alcohols include those selected from the group consisting of $C_{12}$, $C_{13}$, $C_{14}$, $C_{15}$, $C_{16}$, $C_{17}$, $C_{18}$, $C_{19}$, $C_{20}$, $C_{21}$, and $C_{22}$. References here to carbon chain lengths are in relation to each chain, separately, of the diester.

A highly preferred alcohol phosphate diester is dicetylphosphate (CAS-No. 2197-63-9, otherwise known as dihexadecyl phosphate) which is commercially available.

The alkoxyether phosphate or monoester phosphate of an alkoxylated fatty alcohol of the composition is preferably one or a mixture of monoester phosphates of alkoxylated fatty alcohols or alkoxyether phosphates containing from about 12 to about 22 carbon atoms, preferably between 13 to 20 carbon atoms, more preferably between 14 to 18 carbon atoms.

The monoester phosphate of an alkoxylated fatty alcohol is preferably alkoxylated with from about 1 to about 50 moles of an alkylene oxide (per mole of alkoxylated fatty alcohol), the alkylene oxide preferably being selected from for example ethylene oxide, propylene oxide and mixtures thereof.

A highly preferred monoester phosphate of an alkoxylated fatty alcohol is ceteth-10 phosphate (CAS-No. 50643-20-4, otherwise known as 2-hexadecoxyethyl dihydrogen phosphate) which is commercially available.

In one embodiment, the composition comprises a mixture of the mono-ester phosphate of an alkoxylated fatty alcohol with an alcohol phosphate diester of a non-alkoxylated fatty alcohol. The ratio of mono-ester phosphate of alkoxylated fatty alcohol to alcohol phosphate diester of non-alkoxylated fatty alcohol is of from 1:10 to 10:1, more preferably of from 1:9 to 3:1.

Suitable phosphate esters may be formed by reacting alkoxylated or non-alkoxylated fatty alcohols with phosphorous pentoxide ($P_2O_5$) which is a well understood reaction in this field and would be familiar to one of skill in the art.

In one preferred embodiment, the composition of the invention comprises an ionic precipitating agent, a mixture of cetyl and stearyl alcohols (optionally in the form of cetostearyl alcohol), dicetyl phosphate and ceteth-10 phosphate.

When the composition includes all of cetostearyl alcohol, dicetyl phosphate and ceteth-10 phosphate these can be conveniently included in the composition in the form of the commercially available formulation Crodafos™ CES.

In one embodiment, the viscous thixotropic haemostatic gel composition consists or consists essentially of an ionic precipitating agent, cetostearyl alcohol, dicetyl phosphate and ceteth-10 phosphate. The ionic precipitating agent may be as described for the first or third aspects of the invention.

Preferably the Crodafos™ CES (i.e. the combined cetostearyl alcohol, dicetyl phosphate and ceteth-10 phosphate) is included in the composition from 5% to 25%, more preferably 10%-15% by weight of the composition. The dilution of the ionic mixture by the addition of a volume of Crodafos™ CES may be countered by the addition of more of the ionic salt in proportion to the final chosen dilution. In the case of Monsel's solution this is made with ferric subsulphate.

The use of Crodafos™ in the composition of the invention is highly advantageous as it is stable over a wide pH range. Monsel's solution has a very low pH of about 0.5, or less, which presents very unique challenges to the formulating agents chosen. The gelling agents normally used in compositions for topical application of pharmaceuticals are unsuitable for use with these solutions because the acidity causes decomposition of gelling agents such as cellulose derivatives, gums starches, PVP, bentonites and silicon dioxides or is simply incompatible with gel formation by other agents (e.g. Carbopol). The prior art provides no indication that the compositions described herein and, in particular, Crodafos™ would actually be compatible with such highly acidic solutions and indeed the fact that they are not only compatible but they additionally provide valuable thixotropic properties, to aid in the application of the acidic formulation with swab or the like, was a surprising result.

In addition, the very high concentration of iron (III) in Monsel's solution, and so the strongly ionic and high osmotic potential solution, is incompatible with gel formation with materials such as agar or silicate salts which would react with the basic ferric sulphate. The rather unique combination of characteristics of low pH, high ionic strength, high iron (III) concentratoiona do high osmotic potential make it extremely difficult to confidently predict what will happen upon blending it even with components which are well established for their use in other fields.

Other gelling agents that have been used such as starch or glycerin often harbour, contain or aid in the transfer of harmful micro-organisms. Starch is particularly notorious for this whereas the present inventive composition, using Crodafos™, has been shown in a preservative efficacy test to have zero growth of bacteria and so there is no requirement for an additional preservative to be added to the mixture thereby increasing both cost and complexity. Many formulations using starch or glycerin will recommend use of a preservative due to concerns over micro-organism growth and transmission. Further, the present inventor, in experimenting, found that glycerin does not form a suitably viscous and certainly not a thixotropic gel. It is believed that glycerine will degrade with time in the highly acidic environment caused by Monsel's solution. Film formation with polyvinyl pyrrolidone has also been utilized for wounds, but this carries the serious risk of sealing the wound off, thus potentially encouraging anaerobic bacterial proliferation in the wound.

In one embodiment, the viscous thixotropic, haemostatic composition of the present invention is free or substantially free of glycerin and/or polyvinyl pyrrolidone.

The composition of the invention made using Crodafos™ CES is extremely easy to apply topically and shows a greatly reduced tendency to spread from the desired application area or to crystallise out on storage, as compared with the un-gelled solutions. Surprisingly, even given its viscous nature, the presence of the Crodafos™ CES does not interfere with the haemostatic activity of the ionic protein precipitating agent and, importantly, microbial analysis of the compositions of the invention shows that there is no presence or growth of bacteria based on total aerobic plate counts. This is an extremely important advantage over those compositions which may employ starch or glycerin and which are known to be problematic in that they commonly have bacterial contamination which is attributed to or enhanced by the starch and/or glycerin components of the mixture. This can make the application of such compositions to open wounds, generally the intended use, extremely dangerous due to the risk of infection and sepsis.

The composition of the invention can also include a local anaesthetic or mixture of local anaesthetics. Any local anaesthetic or mixtures thereof suitable for the purpose can be included in the composition. For example, the local anaesthetic/s can be of the amide types such as articaine, lidocaine, bupivacaine, levobupivacaine mepivacaine, prilocaine, ropivacaine or oxetacaine; ester types based on benzoic acid such as amylocaine or cocaine; ester types based on meta-aminobenzoic acid such as proxymetacaine; ester types based on para-aminobenzoic acid such as benzocaine, procaine, tetracaine and oxybuprocaine or those fitting into a miscellaneous group including but not limited too: dyclonine, ketocaine, octacaine and diperidon.

Where Monsel's Solution is used in the composition, a convenient and useful anaesthetic to include is the acid stable anaesthetic, oxetacaine. The resultant composition of the invention may be especially beneficial when the application is made to a sensitive or well enervated area such as the treatment of vulval wounds or haemorrhoids. The choice of the topical anaesthetic may be based on its pH activity and/or stability or the clinical outcome to be obtained.

According to a second aspect, there is provided a viscous thixotropic haemostatic gel composition for use in promoting haemostasis at a site of blood loss in a patient in need thereof wherein the viscous thixotropic haemostatic gel composition comprises an ionic precipitating agent, a fatty alcohol, an alcohol phosphate diester and one of an alkoxyether phosphate or a monoester phosphate of an alkoxylated fatty alcohol.

The components of composition are exactly as already described for the first aspect.

For the first and second aspects of the invention, the blood loss may be caused by damage to the skin of the patient, such as would be caused by a surgical procedure such as curettage, colposcopy and biopsy, or damage to 'internal' tissue such as in dental procedures or as may occur naturally in, for example, uterine or haemorrhoidal bleeding. That is, the blood loss need not be caused by an external action such as those of a surgeon or through an accidental trauma but may also be due to natural processes such as vaginal or haemorrhoidal bleeding.

The mode of administration to the site of bleeding may be via a range of means and will depend on the extent of the bleeding, the size of the trauma area and the nature of the tissue to which the composition is being applied. Common means of application known in the art would be suitable. The composition may be applied directly to the site of trauma in the case of damage to the skin such as in a biopsy or may be applied to the site closest to the source of the blood loss such as in uterine applications to thereby stem the blood loss.

The compositions of the invention can be dispensed and delivered in any practicable manner. Preferably and conveniently, the composition can be dispensed into unit dose containers. Unit dose containers may be preferred as multi-dose containers have been implicated in the transfer of micro-organisms between patients, especially if the haemostatic agent was viscosed with a starch or other agent that may maintain or assist the growth of micro-flora. This is a particular problem where the haemostatic agent was used on surfaces within the rectal or genital area or other places which inherently harbour a large micro-flora, although the compositions of the invention show greatly reduced tendency to harbour and spread bacteria.

The unit dose or multi-dose container can be any form commonly in use including, but not limited too: bottles, jars, plastic ampoules, sprays, moulded plastic devices or unit dose containers, squeeze tubes and sachets. The individual containers should be resistant to the composition of the invention. They may be squeezable to extrude the composition, or they may be able to be adapted to hold or attach an applicator to apply the composition to or into difficult locations or into folds of mucous membranes.

The composition of the invention can also be formulated as a soft mouldable gel-like plug for insertion into deeper wounds or mucous crevices. It may be formulated into a spray container or device.

Examples of other methods of delivery of the composition of the invention and appropriate devices can include impregnating the composition into sterile or non sterile bandages (wet or dry), films, suppositories, tampons, collagen packs, hydroxyapatite, acrylate or hyaluronic acid polymers and structures, tubes, and other implantable devices (for example, tooth shaped gels or plugs to stop bleeding post removal of teeth) to enable the composition to reach the site where haemostasis is required. The fact that the present compositions are thixotropic in nature provide great advantages in application. They can be more precisely applied, especially important in delivery to sensitive tissues such as inside the vagina, with less chance of the acidic composition being accidentally spilled or applied to unintended areas.

According to a third aspect, the invention resides in a viscous thixotropic haemostatic gel composition comprising (i) an ionic precipitating agent comprising a polyvalent metal ion wherein the metal is selected from the group consisting of iron, silver, aluminium, calcium, magnesium and manganese; (ii) a fatty alcohol; (iii) an alcohol phosphate diester; and (iv) one of an alkoxyether phosphate or a monoester phosphate of an alkoxylated fatty alcohol.

The use of an ionic precipitating agent which comprises a polyvalent metal ion, wherein the metal is selected from the group consisting of iron, silver, aluminium, calcium, magnesium and manganese, is highly preferred.

In one particularly preferred embodiment, the metal is selected from the group consisting of iron, silver and aluminium.

Preferably, the metal is iron which is provided in the form of an iron salt. Suitable iron salts include ferric chloride and ferric sulphate salts. Particularly preferred is ferric subsulphate. This can be included in the composition in the form of Monsel's solution.

The fatty alcohol, alcohol phosphate diester, and one of an alkoxyether phosphate or a monoester phosphate of an alkoxylated fatty alcohol are as described for the first aspect of the invention.

According to a fourth aspect, there is provided a use of a viscous thixotropic haemostatic gel composition comprising an ionic precipitating agent, a fatty alcohol, an alcohol phosphate diester and one of an alkoxyether phosphate or a monoester phosphate of an alkoxylated fatty alcohol in the manufacture of a medicament for the promotion of haemostasis at a site of blood loss in a patient.

The components of composition are exactly as already described for the first aspect or the third aspect.

The viscous thixotropic haemostatic gel composition may be combined with various emollients or excipients as are known in the art or may comprise only the recited components.

According to a fifth aspect, the invention resides in a kit comprising the viscous thixotropic haemostatic gel composition of the third aspect and an applicator device.

The device can be any device that ensures correct and targeted delivery of the viscous thixotropic haemostatic composition. Examples of appropriate devices include applicators which attach to a single- or multi-dose container of the composition, bandages, sprays and tubes.

The kit may also be supplied in a sterile form to allow safer use within operating theatres or emergency settings.

According to a sixth aspect, the invention resides in a method of formulating the viscous thixotropic haemostatic composition of the third aspect including the step of combining an ionic precipitating agent comprising a polyvalent metal ion wherein the metal is selected from the group consisting of iron, silver, aluminium, calcium, magnesium and manganese with a fatty alcohol, an alcohol phosphate diester and one of an alkoxyether phosphate or a monoester phosphate of an alkoxylated fatty alcohol.

The components may be mixed in the relative amounts or by weight by weight amounts as discussed in relation to the first and third aspects.

The compositions of the invention are advantageously thixotropic, that is, the viscosity is reduced when they are subjected to any shear. This is a very useful property for application of the compositions as the shaking of the container or extrusion from a tube reduces the viscosity of the composition, making either the pickup of the gel onto a swab or extrusion via an applicator easy, targeted and reproducible. Similarly, for preparation of a bandage containing the composition of the invention, application and subsequent rolling or pushing movement of the bandage with the composition applied allows better and more even distribution. This property also makes preparation and filling of containers of the composition easier.

In addition, use of Crodafos™ CES in the compositions of the invention results in a greatly reduced tendency of the precipitating agent to crystallise, even on prolonged standing at reduced temperatures. The composition also shows a reduced tendency to dry out.

The invention therefore provides a viscous thixotropic haemostatic composition which enables easy, reproducible and safe application to any wound site. The composition is stable and shows a great reduction in tendency to harbour and transfer bacteria between patients.

Embodiments of the present invention comprise a viscous thixotropic haemostatic composition. Elements of the invention are illustrated in the following examples, showing only those specific details that are necessary to the understanding of the embodiments of the present invention, but, so as not to clutter the disclosure with excessive detail that will be obvious to those of ordinary skill in the art in light of the present description.

Example 1

Preparation of the Haemostatic Agent—Monsel's Solution

1. Sulphuric acid (55 ml) is added to distilled water (800 ml) in a suitable vessel and the mixture is heated to about 100° C.

2. Nitric acid (75 ml) is added to the solution.
3. Ferrous (II) sulphate heptahydrate (1045 g) in coarse powder form is added in four approximately equal portions sequentially, with stirring after each addition until the effervescence ceases.
4. If, after all the ferrous sulphate has been added, the solution is black, nitric acid is added, a few drops at the time with heating and stirring until the black colour has disappeared and red fumes are no longer evolved.
5. The solution is boiled until it assumes a red colour and free nitrate can no longer be detected.
6. The volume of the mixture is made up to about 1000 ml by addition of distilled water.
7. The solution is cooled, adjusted in volume if necessary to 1000 ml, and, if necessary, filtered to remove any suspended solid.
8. The resulting solution is assayed for iron (III) and the weight per ml is determined. This is expected to be equivalent to 22.2% Fe ions.
9. The solution may then be diluted, if necessary, using water and/or sulphuric acid to obtain the required strength.
10. A solution containing for example 15 to 20 g of iron (III) per 100 ml may be used for the next step.

Example 2

Preparation of a Composition of the Invention Based on Monsel's Solution

1. A solution of 100 mL Monsel's Solution (haemostatic agent from Example 1, assuming dilution to 20% ferric ion) is warmed to 60° C. in a glass container with mild stirring.
2. While the solution is still warm and with stirring, 10% Crodafos™ CES is added and the stirring continued until all the material is dissolved into the solution.
3. The solution's ferric ion level is adjusted upward for the diluting effect of 10% Crodafos™ CES by adding a further 8.3 g of anhydrous ferric sulphate.
4. The solution is then stirred vigorously with mild heat until dissolution.
5. The solution is cooled and assayed for the ferric ion content and any required adjustment made.
6. The composition is dispensed into unit- or multi-dose containers.

Example 3

Viscous Haemostatic Agent Based on Monsel's Solution with an Anaesthetic

1. A solution of 100 mL Monsel's Solution (haemostatic agent from Example 1, assuming dilution to 20% ferric ion) is warmed to 60° C. in a glass container with mild stirring.
2. While the solution is still warm and with stirring, 10% Crodafos™ CES is added and the stirring continued until all the material is dissolved into the solution.
3. The solution's ferric ion level is adjusted upward for the diluting effect of 10% Crodafos™ CES by adding a further 8.3 gm of anhydrous ferric sulphate.
4. The solution is then stirred vigorously with mild heat until dissolution.
5. Oxetacaine base equivalent to 0.2% is added with stirring.
6. The solution is cooled and assayed for the ferric ion and oxetacaine content and any required adjustment made.
7. The composition is dispensed into unit- or multi-dose containers.

The above description of various embodiments of the present invention, is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this patent specification is intended to embrace all alternatives, modifications and variations of the present invention that have been discussed herein, and other embodiments that fall within the spirit and scope of the above described invention.

In this patent specification, adjectives such as first and second, left and right, front and back, top and bottom, etc., are used solely to define one element or method step from another element or method step without necessarily requiring a specific relative position or sequence that is described by the adjectives. Words such as "comprises" or "includes" are not used to define an exclusive set of elements or method steps. Rather, such words merely define a minimum set of elements or method steps included in a particular embodiment of the present invention.

The reference to any prior art in this specification is not, and should not be taken as, an acknowledgement or any form of suggestion that the prior art forms part of the common general knowledge.

The invention claimed is:

1. A viscous thixotropic haemostatic gel composition comprising (i) an ionic precipitating agent substantially in aqueous solution within the composition comprising a polyvalent metal salt selected from an iron sulphate and an iron chloride; (ii) a fatty alcohol; (iii) an alcohol phosphate diester; and (iv) one of an alkoxyether phosphate or a monoester phosphate of an alkoxylated fatty alcohol and wherein the gel composition has a pH of less than 2.5 and comprises between about 15% to about 25% w/v iron (III) ions.

2. The composition of claim 1 wherein the iron sulphate is ferric subsulphate and the iron chloride is ferric chloride.

3. The composition of claim 2 wherein the ferric subsulphate is present in the form of Monsel's solution.

4. The composition of claim 1 wherein the fatty alcohol is selected from the group consisting of myristyl alcohol, pentadecyl alcohol, cetyl alcohol, heptadecyl alcohol, stearyl alcohol, nonadecyl alcohol and arachidyl alcohol.

5. The composition of claim 1 wherein the alcohol phosphate diester is a diester phosphate of a non-alkoxylated fatty alcohol having from 12 to 22 carbon atoms.

6. The composition of claim 5 wherein the alcohol phosphate diester is dicetylphosphate.

7. The composition of claim 1 wherein the monoester phosphate of an alkoxylated fatty alcohol comprises between 12 to 22 carbon atoms.

8. The composition of claim 7 wherein the monoester phosphate of an alkoxylated fatty alcohol is alkoxylated with from about 1 to about 50 moles of an alkylene oxide per mole of alkoxylated fatty alcohol.

9. The composition of claim 8 wherein the alkylene oxide is ethylene oxide and/or propylene oxide.

10. The composition of claim 8 wherein the monoester phosphate of an alkoxylated fatty alcohol is ceteth-10 phosphate.

11. The composition of claim 1 wherein the composition comprises a mixture of the monoester phosphate of an alkoxylated fatty alcohol and an alcohol phosphate diester of a non-alkoxylated fatty alcohol.

12. The composition of claim 1 wherein the composition comprises an ionic precipitating agent comprising ferric subsulphate, cetostearyl alcohol, dicetyl phosphate and ceteth-10 phosphate.

13. The composition of claim 12 wherein the cetostearyl alcohol, dicetyl phosphate and ceteth-10 phosphate comprise from 5% to 25% by weight of the composition.

14. The composition of claim 2 wherein the pH of the composition is less than or about 0.5.

15. A viscous thixotropic haemostatic gel composition comprising (i) ferric subsulphate, present in the composition in the form of Monsel's solution, as an ionic precipitating agent; (ii) cetostearyl alcohol; (iii) dicetyl phosphate; and (iv) ceteth-10 phosphate, and wherein the gel composition has a pH of less than or about 0.5 and comprises between about 15% to about 25% w/v iron (III) ions.

16. A method of promoting haemostasis in a patient in need thereof, comprising, administering to a site of blood loss in the patient a viscous thixotropic haemostatic gel composition of claim 1, thereby promoting haemostasis in the patient.

17. The method of claim 16 wherein the iron sulphate is ferric subsulphate and the iron chloride is ferric chloride.

18. The method of claim 17 wherein the ferric subsulphate is present in the form of Monsel's solution.

19. The method of claim 16 wherein the fatty alcohol is selected from the group consisting of myristyl alcohol, pentadecyl alcohol, cetyl alcohol, heptadecyl alcohol, stearyl alcohol, nonadecyl alcohol and arachidyl alcohol.

20. The method of claim 16 wherein the alcohol phosphate diester is a diester phosphate of a non-alkoxylated fatty alcohol having from 12 to 22 carbon atoms.

21. The method of claim 20 wherein the alcohol phosphate diester is dicetylphosphate.

22. The method of claim 16 wherein the monoester phosphate of an alkoxylated fatty alcohol comprises between 12 to 22 carbon atoms.

23. The method of claim 22 wherein the monoester phosphate of an alkoxylated fatty alcohol is alkoxylated with from about 1 to about 50 moles of an alkylene oxide per mole of alkoxylated fatty alcohol.

24. The method of claim 23 wherein the alkylene oxide is ethylene oxide and/or propylene oxide.

25. The method of claim 23 wherein the monoester phosphate of an alkoxylated fatty alcohol is ceteth-10 phosphate.

26. The method of claim 16 wherein the composition comprises a mixture of the monoester phosphate of an alkoxylated fatty alcohol and an alcohol phosphate diester of a non-alkoxylated fatty alcohol.

27. The method of claim 16 wherein the composition comprises an ionic precipitating agent comprising ferric subsulphate, cetostearyl alcohol, dicetyl phosphate and ceteth-10 phosphate.

28. The composition of claim 27 wherein the cetostearyl alcohol, dicetyl phosphate and ceteth-10 phosphate comprise from 5% to 25% by weight of the composition.

29. The method of claim 16 wherein the blood loss is caused by a surgical procedure selected from the group consisting of a curettage, colposcopy and biopsy or a dental procedure or uterine or haemorrhoidal bleeding.

* * * * *